(12) United States Patent
Hayam et al.

(10) Patent No.: US 11,523,875 B2
(45) Date of Patent: Dec. 13, 2022

(54) ENHANCED CATHETER NAVIGATION METHODS AND APPARATUS

(71) Applicant: Biosense Webster (Israel) Ltd., Yokneam (IL)

(72) Inventors: Gal Hayam, Tivon (IL); Tal Haim Bar-on, Kiriat Tivon (IL); Michael Maydel, Haifa (IL); Shiran Eliyahu, Yokneam Illit (IL); Wagdi Hani Hagla, Julis Village (IL); Aharon Turgeman, Zichron Ya'acov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 436 days.

(21) Appl. No.: 16/840,959

(22) Filed: Apr. 6, 2020

(65) Prior Publication Data

US 2021/0307862 A1    Oct. 7, 2021

(51) Int. Cl.
    *G06K 9/00* (2022.01)
    *G01C 21/00* (2006.01)
    (Continued)

(52) U.S. Cl.
    CPC .............. *A61B 90/37* (2016.02); *A61B 34/20* (2016.02); *A61B 34/25* (2016.02); *G01C 21/20* (2013.01); *G06T 7/0012* (2013.01); *A61B 2034/2055* (2016.02); *A61B 2090/0811* (2016.02); *A61B 2090/364* (2016.02);
    (Continued)

(58) Field of Classification Search
    CPC .................................. G06K 9/00; G01C 21/00
    USPC ........ 382/100, 103, 106–107, 128–133, 154, 382/162, 168, 173, 181, 199, 219, 224, 382/254, 285–291, 305, 321; 600/164, 600/194, 484; 378/4, 21; 701/436, 519
    See application file for complete search history.

(56) References Cited

U.S. PATENT DOCUMENTS

3,871,360 A  *  3/1975 Van Horn ............. G01T 1/1648
                                                      600/484
8,290,228 B2 * 10/2012 Cohen ..................... G06T 11/60
                                                      382/199
(Continued)

*Primary Examiner* — Seyed H Azarian
(74) *Attorney, Agent, or Firm* — Volpe Koenig (57) ABSTRACT

Methods, apparatus, and systems are provided for facilitating the navigation of a catheter between first and second locations within a subject based on display of serial images corresponding to positions of the catheter at successive incremental times. Image production includes sensing catheter positions to produce location data for each time increment. For each position $P_i$, the corresponding location data is processed to respectively produce an image $I_i$ reflecting the position of the catheter at a time $T_i$. Each image $I_i$ is successively displayed at a time equal to $T_i+d$, where d is an image processing visualization delay. Upon a condition that the catheter is displaced to a selected interim location between the first and second locations, the processing of the location data is switched from being performed by a first process associated with a first visualization delay to a second process associated with a second different visualization delay.

20 Claims, 6 Drawing Sheets

(51) Int. Cl.
*A61B 90/00* (2016.01)
*A61B 34/20* (2016.01)
*A61B 34/00* (2016.01)
*G01C 21/20* (2006.01)
*G06T 7/00* (2017.01)

(52) U.S. Cl.
CPC ............ *A61B 2090/3782* (2016.02); *G06T 2207/20024* (2013.01); *G06T 2207/30021* (2013.01); *G06T 2207/30048* (2013.01)

(56) References Cited

U.S. PATENT DOCUMENTS

| | | | |
|---|---|---|---|
| 9,888,973 B2 * | 2/2018 | Olson | A61B 34/30 |
| 11,197,651 B2 * | 12/2021 | Cohen | A61B 5/7289 |
| 2013/0172906 A1 | 7/2013 | Olson | |
| 2013/0178711 A1 * | 7/2013 | Avneri | A61B 17/3403 |
| | | | 604/164.13 |
| 2016/0000446 A1 * | 1/2016 | Eliason | A61M 25/04 |
| | | | 606/194 |

* cited by examiner

ENHANCED CATHETER NAVIGATION METHODS AND APPARATUS

FIELD OF INVENTION

The present application provides systems, apparatuses, and methods for improving medical procedures.

BACKGROUND

Medical conditions such as cardiac arrhythmia (e.g., atrial fibrillation (AF)) are often diagnosed and treated via intra-body procedures. For example, electrical pulmonary vein isolation (PVI) from the left atrial (LA) body is performed using ablation for treating AF. Pulmonary vein isolation, and many other minimally invasive catheterizations, require visualization and mapping of an intra-body surface.

Visualization of intra-body surfaces can be performed by mapping propagation of activation waves. Fluoroscopies, computerized tomography (CT) and magnetic resonance imaging (MRI), as well as other techniques may require a greater than desirable amount of time or resources to provide the visualization and mapping. Additionally, graphical renderings used to visualize intra-body surfaces may not include a sufficient amount of detail when compared to other modes of visualization.

SUMMARY

Methods, apparatus, and systems for medical procedures are disclosed herein. In one example, a method for facilitating the navigation of a distal end of a catheter or the like from a first location within a subject to a second location within the subject with reference to images reflecting relative positions of the distal catheter end as the distal catheter end is displaced from the first location to the second location is provided. The method includes displaying a series of images, each corresponding to a position of the distal catheter end at a successive time increment, as the distal catheter end is displaced from the first location to the second location based on a selected time increment.

The image production generally includes sensing the location of the distal end of the catheter at one or more selected rates to produce location data of the catheter corresponding to a position $P_i$ of the catheter distal end at a time $T_i$ for each time increment. For each position $P_i$, the location data corresponding to the position $P_i$ is processed to respectively produce an image $I_i$ reflecting the position of the distal catheter end at the time $T_i$. Each image $I_i$ is successively displayed at a time equal to $T_i+d$, where d is a visualization delay that includes the time spent to process the location data corresponding to the position $P_i$ to produce the image $I_i$. As explained below, example processing modes are conducted over a moving window of data samples which window includes the sample at time $T_i$ to produce the image $I_i$.

Upon a condition that the catheter distal end is displaced to a selected interim location between the first and second locations, the processing of the location data corresponding to positions $P_i$ to respectively produce images $I_i$ reflecting the position of the distal catheter end at times $T_i$ for each time increment is switched from being performed by a first process associated with a first visualization delay that produces serial images of catheter movement that have a first characteristic to a second process associated with a second different visualization delay that produces serial images of catheter movement that have a second different characteristic.

The differing serial image characteristics produced by the first and second processes may be the degree to which background movement, such as the movement of a beating heart, is displayed in the serial images reflecting the catheter position. An example time increment of 16.7 ms is provided such that a series of 60 images can be produced reflective of 60 positions $P_i$ each second and the images can be displayed on a 60 Hz monitor at 60 frames per second.

Where the interim and second locations are within a beating heart of the subject, one process of the first and second processes can be selected that is associated with a longer visualization delay that produces images having heartbeat movement removed. Such a process may be referred to as a stable mode. In such case, the other process of the first and second processes is associated with a shorter visualization delay that produces images that reflect heartbeat movement. Such a processed may be referred to as a triggered mode.

The method may include selecting a region including the second location and then sensing an entry position upon entry of the distal catheter end into the selected region as the interim location such that visualization processing is automatically switched from being performed by the first process to being performed by the second process upon entry of the distal catheter end into the selected region.

Alternatively, both first and second processes can be implemented by triggered modes where one process of the first and second processes is associated with a longer visualization delay that produces images that reflect heartbeat movement, and the other process of the first and second processes is associated with a shorter visualization delay that produces images that reflect a greater amount of heartbeat movement produced by the one process.

An example apparatus that performs such methods can include a monitor configured to display a series of images, each corresponding to a position of the distal catheter end at a successive time, as the distal catheter end is displaced from the first location to the second location based on a selected time increment. Sensors configured to sense the location of the distal end of the catheter at one or more selected rates are provided to produce location data of the catheter corresponding to a position $P_i$ of the catheter distal end at a time $T_i$ for each time increment as the distal catheter end is displaced from the first location to the second location. A processor is coupled to the sensors and the monitor and configured to process, for each position $P_i$, the location data corresponding to the position $P_i$ to respectively produce an image $I_i$ reflecting the position of the distal catheter end at the time $T_i$, such that each image $I_i$ is successively displayed at a time equal to $T_i+d$ seconds, where d is a visualization delay that includes the time spent to process the location data corresponding to the position $P_i$ to produce the image $I_i$.

To implement the display of different visualization mode processes, the processor is configured to be able to switch the processing of the location data from being performed by a first process associated with a first visualization delay that produces serial images of catheter movement that have a predetermined characteristic to a second process associated with a second different visualization delay that produces serial images of catheter movement that have a different characteristic.

The example processor configuration is such that upon a condition that the catheter distal end is displaced to a selected interim location between the first and second locations, the processing of the location data corresponding to positions $P_i$ to respectively produce images $I_i$ reflecting the position of the distal catheter end at times $T_i$ can be switched from being performed by the first process to being performed by the second process associated with the second different visualization delay.

The processor can be configured to perform as the first and second processes different process among processes that include processes associated with relatively long visualization delays that produce images having a characteristic of heartbeat movement removed when the first and second locations are within a beating heart of the subject, such as the stable mode described herein, and processes associated with relatively short visualization delays that produce images having characteristics that reflect heartbeat movement when the first and second locations are within a beating heart of the subject, such as the triggered modes described herein.

A processor control may be provided that is configured to enable an operator to manually select a specific visualization process or to designate anatomical regions of a subject where respective specified visualization processes are automatically switched to by the processor upon a condition that the distal end of the catheter enters a designated anatomical region.

An example sampling time increment is 16.7 ms so that the processor is configured to produce a series of 60 images reflective of 60 positions each second and an example monitor is a 60 Hz monitor configured to display images at 60 frames per second.

BRIEF DESCRIPTION OF THE DRAWINGS

A more detailed understanding can be had from the following description, given by way of example in conjunction with the accompanying drawings.

DETAILED DESCRIPTION

According to implementations of the disclosed subject matter, apparatus and methods of providing visualization of a catheter within a subject for medical procedures, diagnostics, mapping or other purposes. The visualization comprises sensing and collecting data, processing it into images reflecting the position of the catheter within the subject's body and displaying serial images on a video monitor so that a physician or other operator who is controlling the movement of the catheter can use the video images to assist in the moving or otherwise operating the distal end of the catheter.

Since the processing of the data into the images is not instantaneous, there is inherently a delay in producing an image of a catheter at a position P within the subject at a time T+d seconds, where d is a visualization delay that includes the time spent to process the data corresponding to the position P of the catheter at time T. The smaller the visualization delay, the closer the images displayed to the catheter operator are to the real time movement of the catheter within the subject by the operator.

In accordance with the teachings of the present invention, more than one mode of processing the sensed data into images are employed. In an example embodiment, two types of catheter visualization modes which can respectively be referred to as stable and triggered. Both are valid ways to navigate the end of a catheter within a subject, provide positional images and place the catheter accurately during a medical procedure.

Where catheter navigation is to be, for example, within a beating heart of the subject to, for example, conduct an ablation procedure, a stable mode type of process can be employed to essentially produce images of the catheter distal end within the subject's heart with the heartbeat movement removed. This can be accomplished by employing various filtering techniques for averaging the sensed data over a relatively large number of data samples, which in turn produces a relatively large visualization delay.

Nevertheless, in navigating the catheter in some anatomical areas or during a challenging catheter maneuver, the catheter operator may desire to see images of the catheter position in closer to real time, i.e. with a shorter visualization delay. Accordingly, in the following example embodiment, three triggered modes of image processing are provided with associated visualization delays that are shorter than the visualization delay of the stable mode image processing. In each of the triggered modes, the serial images produced of the distal end of a catheter within the beating heart of a subject will reflect some of the heartbeat movement dependent upon the extent of data averaging, with the shortest averaging mode having the shortest visualization delay producing images reflecting the greatest amount of heartbeat movement and the longest averaging mode having the longest visualization delay producing images reflecting the least amount of heartbeat movement.

The following paragraphs referencing FIGS. 1-3B, reflect an example of a system and methods for sensing and collecting anatomical and catheter positional data and processing it to construct images of both a subjects anatomical structures and a catheter disposed therein. Thereafter, with reference to FIGS. 4-6, the various averaging modes of filtering the image data are discussed to provide the aforementioned different catheter visualization modes.

According to implementations of the disclosed subject matter, a previously captured ultrasound slice of an area of an organ may be displayed, based on a current location of a catheter. A plurality of ultrasound slices may be captured and stored in memory. The plurality of ultrasound slices may be captured using an ultrasound transducer that traverses different portions of an organ and captures the plurality of ultrasound slices while the ultrasound transducer is in a plurality of corresponding ultrasound transducer positions. After capturing and storing the plurality of ultrasound slices using the ultrasound transducer, a catheter may be inserted into the organ. The catheter's position may be determined and may include a catheter location and a catheter orientation. Alternatively, the catheter's position may be determined and may be based on the voxels that may be occupied by an ultrasound slice if the catheter was an ultrasound transducer collecting the ultrasound slice from the catheter's position. To clarify, as disclosed herein, a live catheter's current position may be determined based on a catheter location and a catheter orientation or, alternatively, may be determined based on occupied voxels.

The catheter's position may be compared to the plurality of ultrasound positions which correspond to the plurality of ultrasound slices. A first ultrasound position may be determined to correspond to the catheter's position and the first ultrasound slice may be selected. The selected ultrasound slice may be provided for display. Notably, the selected ultrasound slice may show the area of the organ that corresponds to the catheter's present position such that a health care professional is able to visually see the area of the organ corresponding to the catheter's present position, by being provided the previously stored ultrasound slice.

Figure 1:
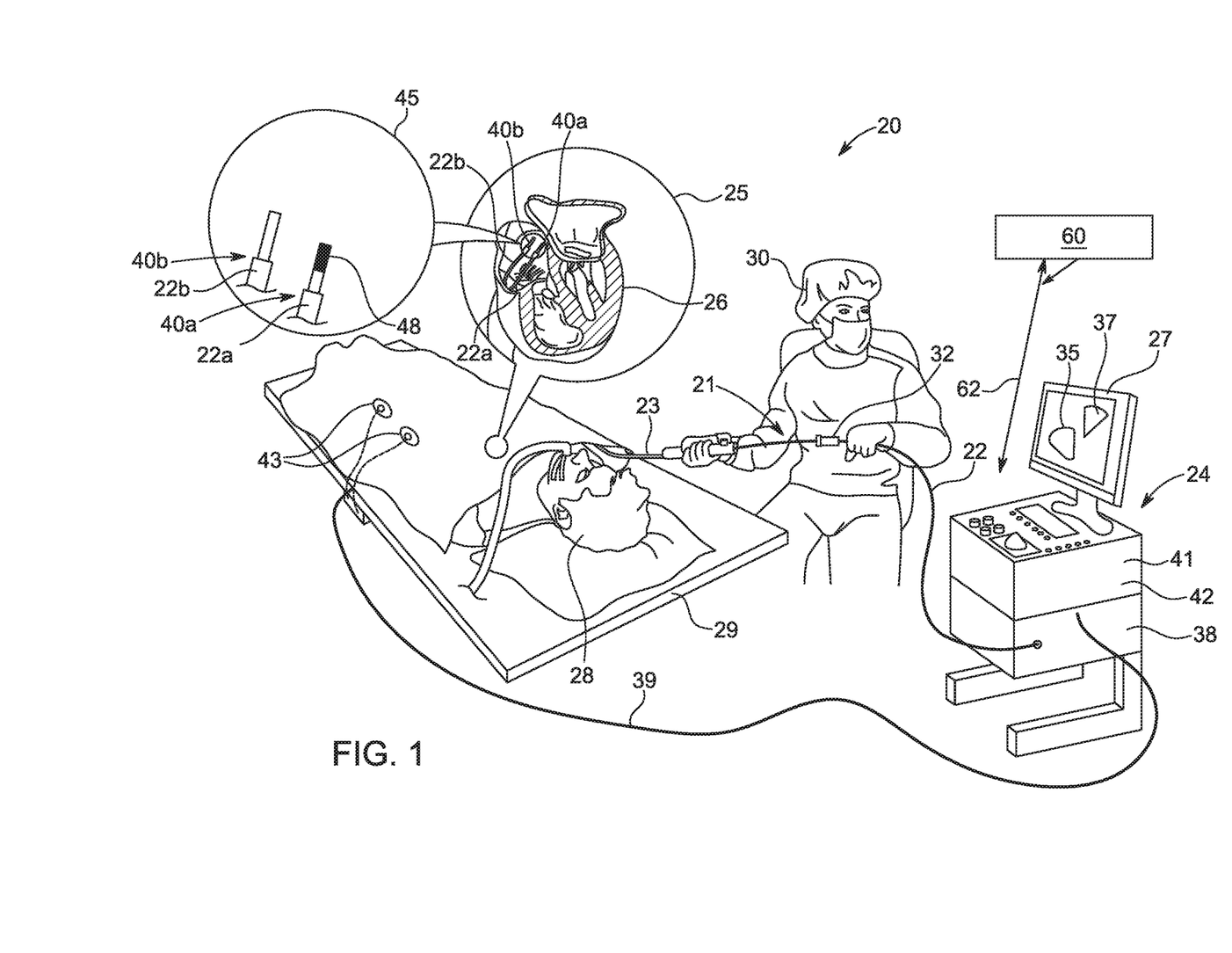
FIG. 1 is a diagram of an exemplary system in which one or more features of the disclosure subject matter can be implemented.

FIG. 1 is a diagram of an exemplary mapping system 20 in which one or more features of the disclosure subject matter can be implemented. Mapping system 20 may include devices, such as a catheter 40a and ultrasound transducer 40b, that are configured to obtain biometric data or ultrasound slices, in accordance with exemplary embodiments of the present invention. The example catheter 40a shown is a point catheter, it will be understood that other catheters may be used to implement the exemplary embodiments of the present invention. Mapping system 20 includes a probe 21, having shafts 22a and 22b that may be navigated by a medical professional 30 into a body part, such as heart 26, of a patient 28 lying on a bed 29. According to exemplary embodiments of the present invention, multiple probes may be provided such that a first probe is in connection with the catheter 40a and a different probe is in connection with the ultrasound transducer 40b. However, for purposes of conciseness, a single probe 21 is described herein but it will be understood that probe 21 may represent multiple probes.

As shown in FIG. 1, medical professional 30 may insert shaft 22a and/or 22b through a sheath 23, while manipulating the distal end of the shafts 22a and/or 22b using a manipulator 32 near the proximal end of the catheter 40a and/or ultrasound transducer 40b and/or deflection from the sheath 23. As shown in an inset 25, catheter 40a and/or ultrasound transducer 40b may be fitted at the distal end of shafts 22a and 22b respectively. Catheter 40a and/or ultrasound transducer 40b may be inserted through sheath 23 in a collapsed state and may be then expanded within heart 26.

According to exemplary embodiments of the present invention, ultrasound transducer 40b may be configured to obtain ultrasound slices of cardiac chamber of heart 26. Inset 45 shows the ultrasound transducer 40b in an enlarged view, inside a cardiac chamber of heart 26. As shown, ultrasound transducer 40b may be attached to shaft 22b.

According to exemplary embodiments of the present invention, catheter 40a may be configured to obtain biometric data of a cardiac chamber of heart 26. Inset 45 shows catheter 40a in an enlarged view, inside a cardiac chamber of heart 26. As shown, catheter 40 may include a point element 48 coupled onto the body of the catheter. According to other exemplary embodiments of the present invention, multiple elements may be connected via splines that form the shape of the catheter 40a. The element 48 may be any elements configured to obtain biometric data and may be electrodes, transducers, or one or more other elements.

According to exemplary embodiments of the present invention, biometric data may include one or more of LATs, electrical activity, topology, bipolar mapping, dominant frequency, impedance, or the like. The local activation time may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. A topology may correspond to the physical structure of a body part or a portion of a body part and may correspond to changes in the physical structure relative to different parts of the body part or relative to different body parts. A dominant frequency may be a frequency or a range of frequency that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part.

As shown in FIG. 1, the probe 21, ultrasound transducer 40b, and catheter 40a may be connected to a console 24. Console 24 may include a processor 41, such as a general-purpose computer, with suitable front end and interface circuits 38 for transmitting and receiving signals to and from catheter 40a and ultrasound transducer 40b, as well as for controlling the other components of mapping system 20. In some exemplary embodiments of the present invention, processor 41 may be further configured to receive biometric data and generate rendering data for a global view and local view, based on the biometric data, as further disclosed herein. According to exemplary embodiments of the present invention, the rendering data may be used to provide the medical professional 30 with a rendering of one or more body parts on a display 27, e.g., a body part rendering 35. According to an exemplary embodiment of the present invention, the processor may be external to the console 24 and may be located, for example, in the catheter, in an external device, in a mobile device, in a cloud-based device, or may be a standalone processor. According to exemplary embodiments of the present invention, the ultrasound transducer 40b may provide ultrasound slices which may be stored in memory 42, as further disclosed herein. The ultrasound transducer 40b may provide the ultrasound slices directly to memory 42 or the ultrasound slices may be provided to processor 41 and the processor 41 may provide the ultrasound slices to memory 42.

As noted above, processor 41 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The example configuration shown in FIG. 1 may be modified to implement the exemplary embodiments of the present invention. The disclosed exemplary embodiments of the present invention may similarly be applied using other system components and settings. Additionally, mapping system 20 may include additional components, such as elements for sensing biometric patient data, wired or wireless connectors, processing and display devices, or the like.

According to an exemplary embodiment of the present invention, a display connected to a processor (e.g., processor 41) may be located at a remote location such as a separate hospital or in separate healthcare provider networks. Additionally, the mapping system 20 may be part of a surgical system that is configured to obtain anatomical and electrical measurements of a patient's organ, such as a heart, and performing a cardiac ablation procedure. An example of such a surgical system is the Carto® system sold by Biosense Webster.

The mapping system 20 may also, and optionally, obtain biometric data such as anatomical measurements of the patient's heart using ultrasound, computed tomography (CT), magnetic resonance imaging (MRI) or other medical imaging techniques known in the art. The mapping system 20 may obtain electrical measurements using catheters, electrocardiograms (EKGs) or other sensors that measure electrical properties of the heart. The biometric data including anatomical and electrical measurements may then be stored in a memory 42 of the mapping system 20, as shown in FIG. 1. The biometric data may be transmitted to the processor 41 from the memory 42. Alternatively, or in addition, the biometric data may be transmitted to a server 60, which may be local or remote, using a network 62. Similarly, ultrasound slices may be transmitted to a server 60, which may be local or remote, using a network 62.

Network 62 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the mapping system 20 and the server 60. The network 62 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 62.

In some instances, the server 60 may be implemented as a physical server. In other instances, server 60 may be implemented as a virtual server a public cloud computing provider (e.g., Amazon Web Services (AWS)®).

Control console 24 may be connected, by a cable 39, to body surface electrodes 43, which may include adhesive skin patches that are affixed to the patient 28. The processor, in conjunction with a current tracking module, may determine position coordinates of the catheter 40a and ultrasound transducer 40b inside the body part (e.g., heart 26) of a patient. The position coordinates may include the location and orientation of catheter 40a and ultrasound transducer 40b. The position coordinates may be based on impedances or electromagnetic fields measured between the body surface electrodes 43 and the electrode 48 or other electromagnetic components of the catheter 40a. Similarly, the position coordinates may be based on impedances or electromagnetic fields measured between the body surface electrodes 43 and the ultrasound transducer 40b. Additionally or alternatively, location pads may be located on the surface of bed 29 and may be separate from the bed 29. The position coordinates may be based on impedances or electromagnetic fields measured between the electrode 48 and/or a component of the ultrasound transducer 40b.

Processor 41 may comprise real-time noise reduction circuitry typically configured as a field programmable gate array (FPGA), followed by an analog-to-digital (A/D) ECG (electrocardiograph) or EMG (electromyogram) signal conversion integrated circuit. The processor 41 may pass the signal from an A/D ECG or EMG circuit to another processor and/or can be programmed to perform one or more functions disclosed herein.

Control console 24 may also include an input/output (I/O) communications interface that enables the control console to transfer signals from, and/or transfer signals to electrode 48 and/or ultrasound transducer 40b and electrodes 43 or a location pad. Based on signals received from electrode 48, ultrasound transducer 40b and/or electrodes 43, processor 41 may generate rendering data that enables a display, such as display 27 to render a body part, such as a body part rendering 35.

During a procedure, processor 41 may facilitate the presentation of a body part rendering 35 and/or an ultrasound slice 37 to medical professional 30 on a display 27, and store data representing the body part rendering 35 and ultrasound slice 37 in a memory 42. Memory 42 may comprise any suitable volatile and/or non-volatile memory, such as random-access memory or a hard disk drive. In some exemplary embodiments of the present invention, medical professional 30 may be able to manipulate a body part rendering 35 and/or ultrasound slice 37 using one or more input devices such as a touch pad, a mouse, a keyboard, a gesture recognition apparatus, or the like. For example, an input device may be used to change the position of catheter 40a such that rendering 35 is updated and a different ultrasound slice 37 is provided based on the updated position, as disclosed herein. In alternative exemplary embodiments of the present invention, display 27 may include a touchscreen that can be configured to accept inputs from medical professional 30, in addition to presenting a body part rendering 35 and ultrasound 37, including a global view and a local view.

According to exemplary embodiments of the present invention, an ultrasound transducer may be configured to capture ultrasound slices at various positions within the intra-body organ. The ultrasound transducer may be the same as or similar to ultrasound transducer 40b of FIG. 1. The ultrasound transducer may be inserted into an intra-body organ, such as a heart 26 of FIG. 1. More specifically, the ultrasound transducer may be inserted into a chamber of in intra-body organ, such as a heart chamber of heart 26. The ultrasound transducer may be configured to automatically capture ultrasound slices at pre-determined intervals of time (e.g., one ultrasound slice per millisecond) or may be configured to capture ultrasound slices based on the position and/or movement of the ultrasound transducer. For example, the ultrasound transducer may be configured to capture up to a given number of ultrasound slices (e.g., three ultrasound slices) per each position of the ultrasound transducer. Accordingly, the ultrasound transducer may be configured to capture multiple ultrasound slices for each ultrasound transducer position. According to an exemplary embodiments of the present invention, a processor, such as processor 41 of FIG. 1, may be configured to select a single ultrasound slice from a plurality of ultrasound slices at the same ultrasound position. The processor may select the single ultrasound slice based one or more factors such as ultrasound slice quality, ultrasound transducer stability while the ultrasound slice is collected, signal to noise ratio, or the like. As an example, an ultrasound slice quality may be determined based on the detected boundaries of the organ within the slice when compared to free space (e.g., a blood pool) of the organ within the slice. A first ultrasound slice may be replaced by a second ultrasound for the same ultrasound position, based on the selection and factors described herein.

As applied herein, an ultrasound position may correspond to either an ultrasound transducer position or an ultrasound slice position, as further described herein. An ultrasound transducer position may be the position of an ultrasound transducer when a given ultrasound slice is captured. The ultrasound transducer position may include an ultrasound transducer location (e.g., coordinates) and an ultrasound transducer orientation (e.g., angle), as further disclosed herein. The ultrasound slice position may correspond to the area, volume, or voxels occupied by the ultrasound slice. As applied herein, a catheter position may correspond to either a catheter location (e.g., coordinates) and orientation (e.g., angle) or may correspond to a catheter slice position, as further disclosed herein.

According to an exemplary embodiment of the present invention, an ultrasound transducer position or a catheter position may include both the location and orientation of the corresponding ultrasound transducer or catheter. A location (i.e., ultrasound transducer position or a catheter position) may be stored as or include coordinates which may be represented as cartesian coordinates, polar coordinates, voxel coordinates, or any other applicable coordinates or a combination thereof. The location may be relative to a reference point which may be internal to the body, internal to an intra-body organ, internal to an intra-body organ chamber or external to the body. The location may be determined based on signals (e.g., electromagnetic signals) from the ultrasound transducer, the catheter, body surface electrodes (e.g., body surface electrodes 43 of FIG. 1), a location pad, or other location-based component.

An orientation may be based on a reference point (e.g., tip) of the ultrasound transducer or catheter such that the orientation indicates the direction that the reference point of the ultrasound transducer and/or catheter is facing. It will be understood that although a reference point is specifically recited herein, the reference point may be a collection of points, such as a line. The reference point may be any part of an ultrasound transducer or catheter such as a distal point, a proximal point, or any other applicable point. The orientation may be stored or include an angle, a phase, a direction, an axis, an elevation, or a combination thereof.

Figure 2:
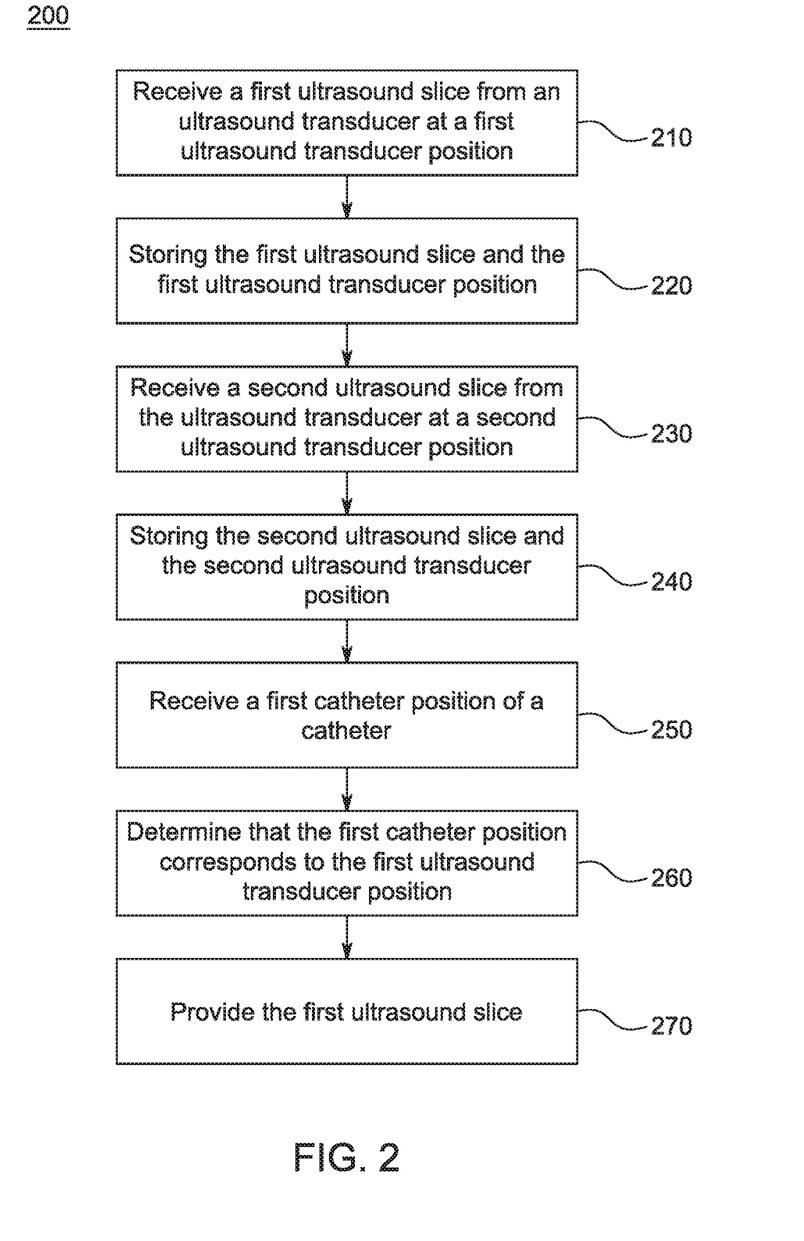
FIG. 2 is a flowchart for providing an ultrasound slice based on a catheter's position.

FIG. 2 shows a process flowchart 200 for providing a previously stored ultrasound slice, from a plurality of previously stored ultrasound slices, based on a catheter's position.

At step 210 of the process illustrated in FIG. 2, a first ultrasound slice may be received from an ultrasound transducer while the ultrasound transducer is in a first ultrasound transducer position. The first ultrasound slice captured while the ultrasound transducer is in a first position may be one of a plurality of slices that are collected while the ultrasound transducer is in the first position. As disclosed herein, a processor may designate a single ultrasound slice from the plurality of ultrasound slices as the first ultrasound slice for a given ultrasound location, based on one or more of ultrasound slice quality, ultrasound transducer stability while the ultrasound slice is collected, signal to noise ratio, or the like.

Figure 3A:
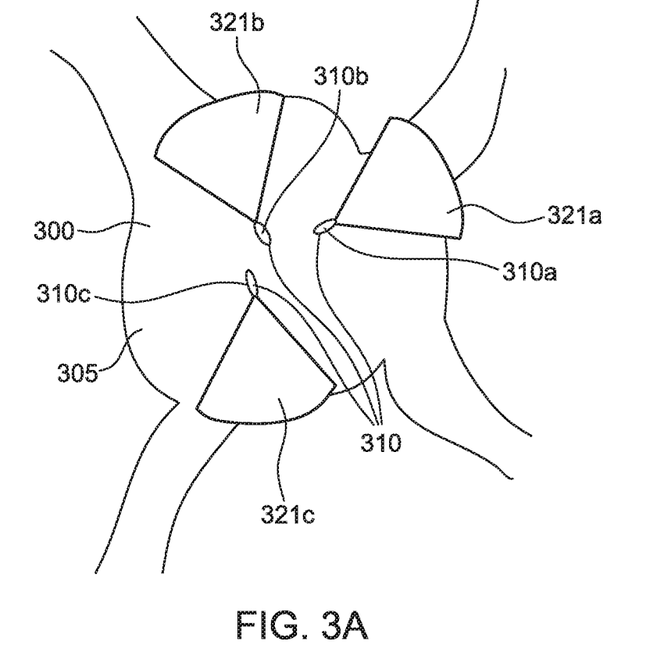
FIG. 3A is an illustration of an ultrasound transducer collecting ultrasound slices at various positions.

FIG. 3A shows an example diagram of a heart chamber 300 with an ultrasound transducer 310 in a plurality of positions 310a, 310b, and 310c. As shown in FIG. 3A, and in accordance with step 210 of the process illustrated in FIG. 2, a first ultrasound slice 321a may be received from the ultrasound transducer 310 while the ultrasound transducer is in a first ultrasound transducer position 310a. The first ultrasound transducer position 310a may be represented by a location (e.g., coordinates) as well as an orientation (e.g., an angle and elevation) such that slice 321a is associated with the first ultrasound transducer position 310a.

At step 220 of the process illustrated in FIG. 2, the first ultrasound slice and the first ultrasound transducer position corresponding to the first ultrasound slice may be stored in any applicable storage medium such as in a memory 42 of FIG. 1. The first ultrasound slice may be stored as an image type file, a video type file, or any other file that enables the first ultrasound slice to be rendered at a time after the first ultrasound slice is captured by the ultrasound transducer. The first ultrasound transducer position may be stored within the same file or group of files that include the first ultrasound slice or may be stored in a separate memory location than the first ultrasound slice such that the stored first ultrasound transducer position and the first ultrasound slice are correlated to each other through any applicable manner such as via a pointer, a lookup table, or the like. In accordance with the example provided in FIG. 3A, the first ultrasound slice 321a and the first ultrasound transducer position 310a may be stored in a memory.

At step 230 of the process illustrated in FIG. 2, a second ultrasound slice may be received from an ultrasound transducer while the ultrasound transducer is in a second ultrasound transducer position. The second ultrasound slice captured while the ultrasound transducer is in a second position may be one of a plurality of slices that are collected while the ultrasound transducer is in the second position, as disclosed herein. A single slice from the plurality of slices collected while the ultrasound transducer is in the second position may be designated as the second ultrasound slice. As shown in FIG. 3A, and in accordance with step 230 of the process illustrated in FIG. 2, a second ultrasound slice 321b may be received from the ultrasound transducer 310 while the ultrasound transducer is in a second ultrasound transducer position 310b. The second ultrasound transducer position 310b may be represented by a location (e.g., coordinates) as well as an orientation (e.g., an angle and elevation) such that slice 321b is associated with the first ultrasound transducer position 310b.

At step 240 of the process illustrated in FIG. 2, the second ultrasound slice and the second ultrasound transducer position corresponding to the second ultrasound slice may be stored in any applicable storage medium such as in a memory 42 of FIG. 1 in a similar manner as that disclosed in accordance with step 220. Although steps 210 through 240 disclose a first ultrasound slice and a second ultrasound slice for simplicity, it will be understood that one or more additional ultrasound slices may be captured and stored. For example, as shown in FIG. 3A, ultrasound slice 321c may be captured while the ultrasound transducer 310 is in an ultrasound transducer position 310c and the corresponding data may be stored in a memory.

At step 250 of the process illustrated in FIG. 2, a first catheter position corresponding to an intra-body catheter may be received. The intra-body catheter may be the same as or similar to the catheter 40a of FIG. 1 and may be inserted into an intra-body chamber either while an ultrasound transducer is in the intra-body chamber or after an ultrasound transducer is removed from the intra-body chamber. The first catheter position may be received via any applicable means including via electromagnetic signals between electrodes on the catheter and a location pad, electromagnetic signals between electrodes on the catheter and body electrodes, etc. The first catheter position may include a location and an orientation, as disclosed herein. According to an implementation of this exemplary embodiment, the first catheter position may be in the same format as the ultrasound transducer positions stored at steps 220 and 240 of FIG. 2. According to another implementation, the first catheter position may be in a different format than the ultrasound transducer positions stored at steps 220 and 240 but may be converted such that they can be correlated with the format of the ultrasound transducer positions stored at steps 220 and 240.

Figure 3B:
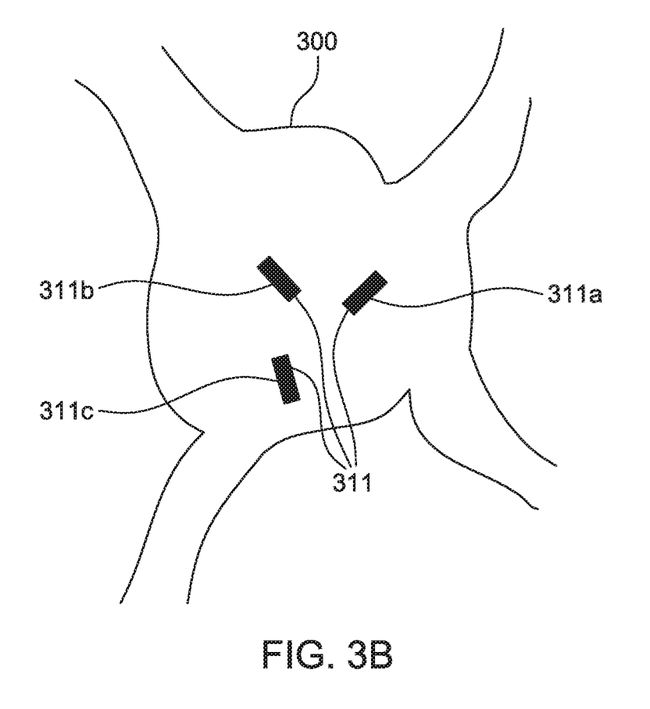
FIG. 3B is an illustration of a catheter at various positions corresponding to the positions of FIG. 3A.

FIG. 3B shows an example diagram of the heart chamber 300 of FIG. 3A with a catheter 311 at various positions 311a, 311b, and 311c. As shown in FIG. 3B, and in accordance with step 250 of the process illustrated in FIG. 2, the catheter's position while the catheter is in the first position 311a may be received. The catheter's position may be updated at pre-determined time intervals or based on detection of movement of the catheter.

At step 260 of the process illustrated in FIG. 2, a determination may be made that the first catheter position received at step 250 corresponds to the first ultrasound transducer position received at step 210 and stored at 220. Although the first catheter position received at step 250 is described as corresponding to the first ultrasound transducer position received at step 210 for simplicity, it will be understood that a catheter position may correspond to any one of the ultrasound transducer position.

The determination that the first catheter position received at step 250 corresponds to the first ultrasound transducer position may be based on comparing the received catheter position (i.e., step 250) to the stored ultrasound transducer positions (i.e., steps 220 and 240). According to an exemplary embodiment of the present invention, the catheter position may be received in the same format as the stored ultrasound transducer positions. For example, the catheter position may include the catheter location which may be received as a set of coordinates and may also include the catheter orientation which may be received as an angle and an elevation. For example, the catheter position may include a location x, y, and z coordinates (4 mm, 8 mm, 1 mm) from a coordinate reference point such as an external patch or an area within an intra-body organ. The catheter position may include an angle 44 degrees corresponding to the horizontal angle of a reference point (e.g., tip) of the catheter and an elevation of 14 degrees corresponding to the vertical angle of the reference point of the catheter. According to this example, the catheter position may be represented as (4, 8, 1, 44, 14). At step 260, the catheter position may be compared to a plurality of ultrasound transducer positions which may be in the same format. For example, the first ultrasound transducer position stored at step 220 may be (5, 8, 1, 44, 14) and the second ultrasound transducer position stored at step 240 may be (6, 8, 1, 44, 14). A calculation may be made as to which of the plurality of stored ultrasound transducer positions is the closest to the received catheter position. Continuing the example, since the catheter position (4, 8, 1, 44, 14) is only 1 mm different than the first ultrasound transducer position (5, 8, 1, 44, 14), it may be determined the first ultrasound transducer position corresponds to the catheter position as the second ultrasound transducer position (6, 8, 1, 44, 14) is 2 mm different than the catheter position.

According to an exemplary embodiment of the present invention, the received catheter position may be in a different format (e.g., polar coordinates instead of cartesian coordinate than the plurality of stored ultrasound transducer positions. It will be understood that one or more of the different formats may be converted such that both sets of positions (catheter positions and ultrasound transducer positions) may be compared to each other to determine which of a plurality of ultrasound transducer positions corresponds to the catheter position.

According to an exemplary embodiment of the present invention, a correlation threshold may be provided such that if the differences between a catheter position and all available ultrasound transducer positions are greater than the correlation threshold then a determination is made that no ultrasound transducer position corresponds to the catheter position. Accordingly, at step 270, as further disclosed herein, no ultrasound slice may be displayed. Notably, in this scenario, there may be no ultrasound slices that would visually show the area that corresponds to a current catheter position and, thus, no ultrasound slice may be provided at step 270.

At step 270 of the process illustrated in FIG. 2, the ultrasound slice (e.g., first ultrasound slice) associated with the ultrasound transducer position (e.g., first ultrasound transducer position) that is determined to correspond to the catheter position, at step 260, may be provided. The ultrasound slice may be provided via a display such as display 27 of FIG. 1. Alternatively, the ultrasound slice may be provided to an external display such as via network 62 and server 60 such that the ultrasound slice may be displayed at a remote location.

For navigating the distal end of a catheter, such as catheter 40a, it is generally desirable to display serial images of the catheter position on the display 27 to the physician 30. Where, for example, an ablation procedure is to be conducted, the navigation includes displacing the catheter distal end within the heart.

As referenced above, the example system is configured to enable the operator 30 to select via the system console 24 any one of several modes of processing that the processor 41 is configured to perform in which to produce serial images of the catheter position which modes reflect different degrees of heartbeat movement. In this example, the selection control in the console 24 is configured to enable the operator 30 to either manually select a specific mode when the operator 30 choses or to designate anatomical regions of a subject where respective specified modes are automatically switched to by the processor upon a condition that the distal end of the catheter enters a designated anatomical region.

In order to implement different visualization modes processes, the processor 41, in this example, is configured to average samples of the sensed position data of the catheter using selected filtering. Each mode employs a different moving window of sample positions. As a result, the mode employing the smallest window has the shortest visualization delay and produces images reflecting the greatest amount of heartbeat movement. The mode employing the largest window has the longest visualization delay and produces images reflecting the least amount of heartbeat movement. The latter being a stable mode where there is essentially no heartbeat movement reflected in the displayed serial images.

In the example embodiment, the processor 41 is configured to implement four different modes for producing the displayed serial images of the catheter position: one stable mode where heartbeat movement is essentially entirely removed and three triggered modes where different degrees of heartbeat movement are reflected in the displayed serial images. In all four modes, a sample size of data accumulated over 16.7 ms (i.e. one sixtieth of a second) is used in conjunction with Gaussian filtering.

For the stable mode, a Gaussian filter of 61 coefficients is employed that implements a moving window of 60 positions which equates to a one second window and the associated visualization delay to produce the serial images reflecting no heartbeat movement is approximately 500 ms. For one triggered mode, Mode 1, a Gaussian filter of 27 coefficients is employed that implements a moving window of 26 positions which equates to a window of about 430 ms and the associated visualization delay to produce the serial images is approximately 216 ms. For a second triggered mode, Mode 2, a Gaussian filter of 21 coefficients is employed that implements a moving window of 20 positions which equates to a window of about 330 ms and the associated visualization delay to produce the serial images is approximately 166 ms. For a third triggered mode, Mode 3, a Gaussian filter of 13 coefficients is employed that implements a moving window of 12 positions which equate to a window of about 200 ms and the associated visualization delay to produce the serial images is approximately 100 ms.

Figure 4:
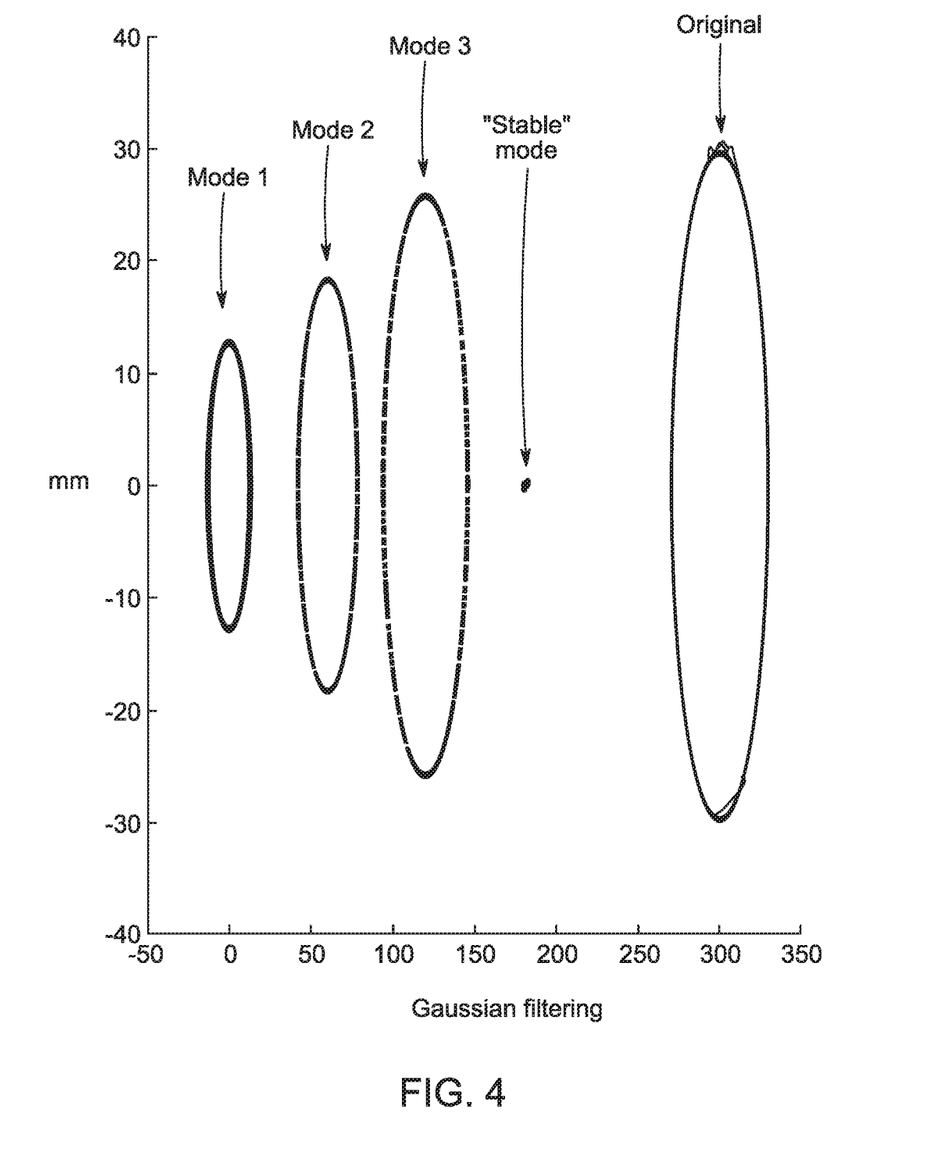
FIG. 4 are comparative graphs of Gaussian filtering with respect to a simulation of a fast (3 Hz) noisy periodical circular catheter movement.
Figure 5:
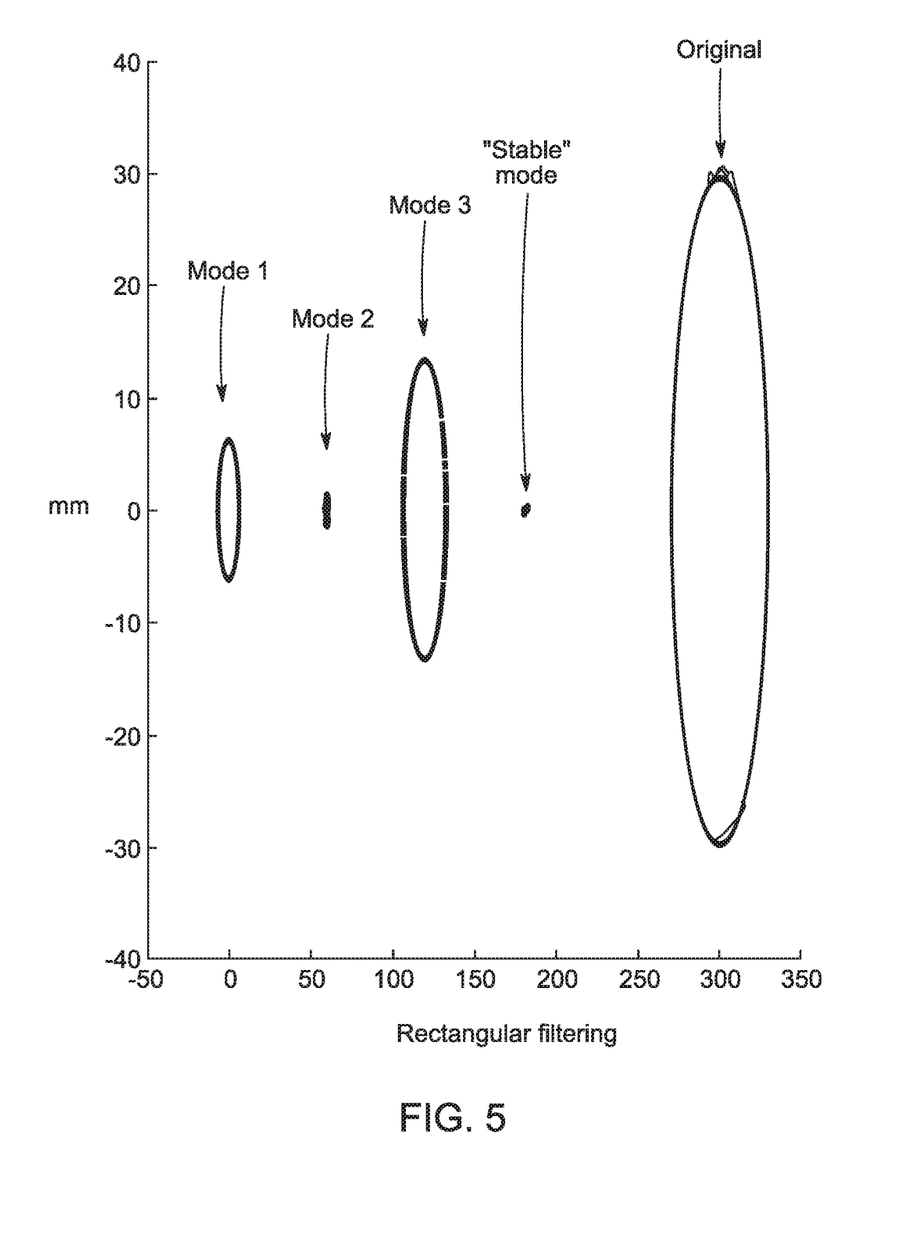
FIG. 5 are comparative graphs of rectangular filtering with respect to a simulation of a fast (3 Hz) noisy periodical circular catheter movement.

Although other filtering techniques can be employed, Gaussian filtering is preferred. FIG. 4 provides comparative graphs of the four visualization modes employing Gaussian filtering with respect to a simulation of a fast (3 Hz) noisy periodical circular catheter movement. FIG. 5 provides comparative graphs of four corresponding visualization modes employing Rectangular filtering with respect to the simulation of the fast (3 Hz) noisy periodical circular catheter movement.

The Rectangular filtering over-averages due to the identical weight for different parts of the period which cancel each other, especially in the Mode 2 filter (21 samples), which matches the period of the movement period. The Gaussian filtering does not suffer from this. Catheter traces are shifted to allow easy viewing. The "stable" mode output is also very attenuated for this particular signal.

Figure 6:
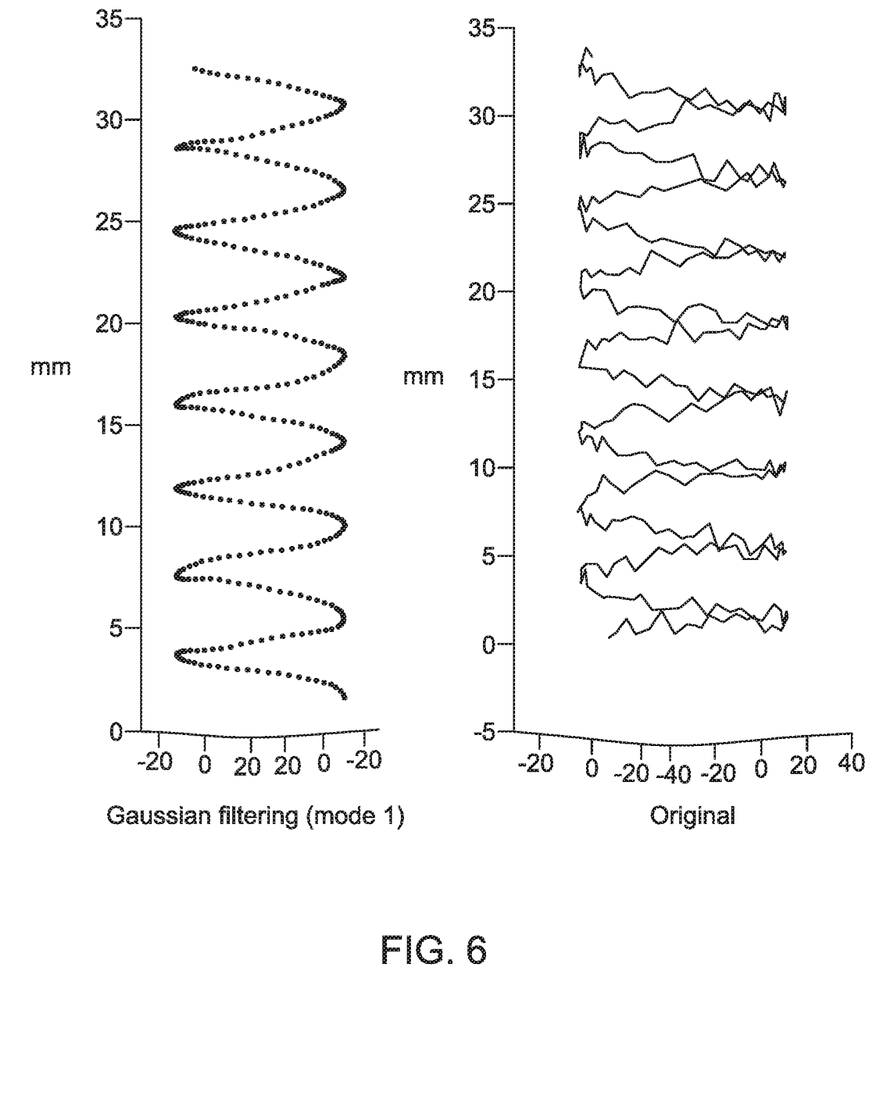
FIG. 6 is a comparative graph of Gaussian filtering with a 27 coefficient window with respect to a simulation of upward movement of a noisy catheter.

FIG. 6 illustrates the relative smoothness of serial images produced by Mode 1 triggered processing by providing a comparative graph of Mode 1 Gaussian filtering with a 27 coefficient window with respect to a simulation of upward movement of a noisy catheter.

Although specific example modes of filtering are described above, the processor 41 can be configured to implement visualization modes having other characteristics. In some systems it may be desirable to change the sampling rate and/or the size of the moving window filter to implement a stable mode. Generally, for filtering modes based on 16.7 ms sampling, it is preferred to provide modes that include applying a Gaussian Filter having a moving window in a range of 12 to 60 positions such that the visualization delay associated with the process is within a respective range of approximately 100 ms to approximately 500 ms.

In, for example, the performance of a heart ablation procedure to be performed at a predetermined ablation location within the subject's heart, the physician 30 will navigate the distal end of an ablation catheter from an initial location to the ablation location to perform ablation. For different segments of catheter movement, the physician 30 can select the visualization mode used to produce the serial images to help the physician 30 guide the catheter movement.

For example, the physician 30 can select to move the catheter from the initial location to an interim location within the subject's heart with reference to displayed serial images of the catheter movement produced by the stable visualization mode. The physician 30 can then select to further move the catheter from the interim location to the ablation location with reference to displayed serial images of the catheter movement produced by a selected one of the triggered visualization modes.

In lieu of moving the catheter from the interim location directly to the ablation location with reference to displayed serial images of the catheter movement produced by the selected triggered visualization mode, the physician 30 can decide to move the catheter from the interim location only as far as a second interim location with reference to displayed serial images of the catheter movement produced by the selected triggered visualization mode. The physician 30 can then select to further move the catheter from the second interim location to the ablation location with reference to displayed serial images of the catheter movement produced by either a different one of the triggered visualization modes or the stable visualization mode.

Generally the process can be described as a method for facilitating the navigation of a distal end of a catheter or the like from a first location within a subject to a second location within the subject with reference to images reflecting relative positions of the distal catheter end as the distal catheter end is displaced from the first location to the second location. The method includes displaying a series of images, each corresponding to a position of the distal catheter end at a successive time increment, as the distal catheter end is displaced from the first location at a time $T_0$ to the second location at a time $T_0+X$ seconds based on a selected time increment.

Navigation of the distal catheter end from the first location to the second location need not be performed by a continuous movement of the distal catheter end, but can include periods where no movement of the catheter is being made by the physician 30.

The image production generally includes sensing the location of the distal end of the catheter at one or more selected rates to produce location data of the catheter corresponding to a position $P_i$ of the catheter distal end at a time $T_i$ for each time increment from $T_0$ to $T_0+X$ seconds. For each position $P_i$, the location data corresponding to the position $P_i$ is processed to respectively produce an image $I_i$ reflecting the position of the distal catheter end at the time $T_i$. Each image $I_i$ is successively displayed at a time equal to $T_i+d$, where d is a visualization delay that includes the time spent to process the location data corresponding to the position $P_i$ to produce the image $I_i$. As explained above, the processing by the example processing modes is conducted over a moving window of data samples which window include the sample at time $T_i$ to produce the image $I_i$.

Upon a condition that the catheter distal end is displaced to a selected interim location at a time $T_0+(X-Y)$ seconds between the first and second locations, the processing of the location data corresponding to positions $P_i$ to respectively produce images $I_i$ reflecting the position of the distal catheter end at times $T_i$ for each $T_i$ from $T_0$ to $T_0+(X-Y)$ seconds is switched from being performed by a first process associated with a first visualization delay that produces serial images of catheter movement that have a first characteristic to a second process associated with a second different visualization delay that produces serial images of catheter movement that have a second different characteristic to produce images $I_i$ corresponding to positions $P_i$ reflecting the position of the distal catheter end at time $T_i$ for each $T_i$ from $T_0+(X-Y)$ seconds to $T_0+X$ seconds. The differing serial image characteristics produced by the first and second processes may be the degree to which background movement, such as the movement of a beating heart, is displayed in the serial images of the catheter position.

As noted above, an example time increment is 16.7 ms so that a series of 60 images are produced reflective of 60 positions $P_i$ each second and the images can be displayed on a 60 Hz monitor at 60 frames per second.

Where the interim and second locations are within a beating heart of the subject, one process of the first and second processes can be selected that is associated with a longer visualization delay that produces images having heartbeat movement removed, such as the stable mode described above. In such case, the other process of the first and second processes is associated with a shorter visualization delay that produces images that reflect heartbeat movement, such as one of the triggered modes described above.

In the example embodiment, the switching between the first and second processes can be made manually by the physician 30 when, for example, the physician views the distal end of the catheter is at the desired interim location. Alternatively, the physician 30 may select a region where the switching between the first and second processes is automatically made when the catheter is sensed as entering into the selected region. For example, the physician 30 may select a specific region in the subject's heart which includes a difficult to reach ablation site. A stable mode process may be implemented while the catheter is displaced before reaching an entry point of the selected region. Upon the catheter being sensed as entering the selected region, the visualization mode in this case will automatically be switched to a triggered mode process to provide the physician 30 a faster visualization of the catheter movement from that entry point to the difficult to reach ablation site.

Both first and second processes can be implemented by triggered modes where one process of the first and second processes is associated with a longer visualization delay that produces images that reflect heartbeat movement, and the other process of the first and second processes is associated with a shorter visualization delay that produces images that reflect a greater amount of heartbeat movement produced by the one process.

Generally, an apparatus that performs such methods can include a monitor configured to display a series of images, each corresponding to a position of the distal catheter end at a successive time, as the distal catheter end is displaced from the first location to the second location based on a selected time increment such as depicted in FIG. 1 above. Sensors, such as described above, configured to sense the location of the distal end of the catheter at one or more selected rates are provided to produce location data of the catheter corresponding to a position $P_i$ of the catheter distal end at a time $T_i$ for each time increment as the distal catheter end is displaced from the first location to the second location. A processor, such as processor 41, is coupled to the sensors and the monitor and configured to process, for each position $P_i$, the location data corresponding to the position $P_i$ to respectively produce an image $I_i$ reflecting the position of the distal catheter end at the time $T_i$, such that each image $I_i$ is successively displayed at a time equal to $T_i+d$ seconds, where d is a visualization delay that includes the time spent to process the location data corresponding to the position $P_i$ to produce the image $I_i$.

To implement the display of different visualization modes, the processor is configured to be able to switch the processing of the location data from being performed by a first process associated with a first visualization delay that produces serial images of catheter movement that have a predetermined characteristic to a second process associated with a second different visualization delay that produces serial images of catheter movement that have a different characteristic.

The example processor configuration is such that upon a condition that the catheter distal end is displaced to a selected interim location between the first and second locations, the processing of the location data corresponding to positions $P_i$ to respectively produce images $I_i$ reflecting the position of the distal catheter end at times $T_i$ can be switched from being performed by the first process to being performed by the second process associated with the second different visualization delay.

The processor can be configured to perform as the first and second processes different process among processes that include processes associated with relatively long visualization delays that produce images having heartbeat movement removed when the first and second locations are within a beating heart of the subject, such as the stable mode described above, and processes associated with relatively short visualization delays that produce images that reflect heartbeat movement when the first and second locations are within a beating heart of the subject, such as the triggered Modes described above.

The sampling time increment is preferably selected to be 16.7 ms so that the processor is configured to produce a series of 60 images reflective of 60 positions each second and the monitor is a 60 Hz monitor configured to display images at 60 frames per second.

Any of the functions and methods described herein can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer-readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general-purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

The invention claimed is:

1. A method for facilitating the navigation of a distal end of a catheter from a first location within a subject to a second location within the subject with reference to images reflecting relative positions of the distal catheter end as the distal catheter end is displaced from the first location to the second location, the method comprising:

displaying a series of images, each corresponding to a position of the distal catheter end at a successive time, as the distal catheter end is displaced from the first location to the second location based on a selected time increment, including:

sensing the location of the distal end of the catheter at one or more selected rates to produce location data of the catheter corresponding to a position $P_i$ of the catheter distal end at a time $T_i$ for each time increment as the distal catheter end is displaced from the first location to the second location;

for each position $P_i$, processing the location data corresponding to the position $P_i$ to respectively produce an image $I_i$ reflecting the position of the distal catheter end at the time $T_i$; and successively displaying each image $I_i$ at a time equal to $T_i$+d seconds, where d is a visualization delay that includes the time spent to process the location data corresponding to the position $P_i$ to produce the image $I_i$; and upon a condition that the catheter distal end is displaced to a selected interim location between the first and second locations, the processing of the location data corresponding to positions $P_i$ to respectively produce images $I_i$ reflecting the position of the distal catheter end at times $T_i$ is switched from being performed by a first process associated with a first visualization delay that produces serial images of catheter movement that have a first characteristic to a second process associated with a second different visualization delay that produces serial images of catheter movement that have a second different characteristic than the serial images produced by the first process, wherein a process that produces images having heartbeat movement removed includes applying a Gaussian Filter.

2. The method of claim 1 where the interim and second locations are within a beating heart of the subject wherein:
one process of the first and second processes is associated with a longer visualization delay that produces images having heartbeat movement removed; and
the other process of the first and second processes is associated with a shorter visualization delay that produces images that reflect heartbeat movement.

3. The method of claim 2 wherein the time increment is selected to be 16.7 ms so that a series of 60 images are produced each second reflective of 60 positions $P_i$.

4. The method of claim 3 wherein:
the one process that produces images having heartbeat movement removed includes applying a Gaussian Filter having a moving window of 60 positions such that the visualization delay associated with the one process is approximately 500 ms; and
the other process that produces images reflecting heartbeat movement includes applying a Gaussian Filter having a moving window in a range of 12 to 26 positions such that the visualization delay associated with the other process is within a respective range of approximately 100 ms to approximately 216 ms.

5. The method of claim 4 wherein the other process that produces images reflecting heartbeat movement is selected from one of the following processes:
a process that includes applying a Gaussian Filter having a moving window of 12 positions such that the visualization delay associated with the other process is approximately 100 ms;
a process that includes applying a Gaussian Filter having a moving window of 20 positions such that the visualization delay associated with the other process is approximately 166 ms; or
a process that includes applying a Gaussian Filter having a moving window of 26 positions such that the visualization delay associated with the other process is approximately 216 ms.

6. The method of claim 1 further comprising:
selecting a region including the second location; and
sensing an entry position upon entry of the distal catheter end into the selected region as the interim location such that visualization processing is automatically switched from being performed by the first process to being performed by the second process upon entry of the distal catheter end into the selected region.

7. The method of claim 1 where the interim and second locations are within a beating heart of the subject wherein:
one process of the first and second processes is associated with a longer visualization delay that produces images that reflect heartbeat movement; and
the other process of the first and second processes is associated with a shorter visualization delay that produces images that reflect a greater amount of heartbeat movement produced by the one process.

8. The method of claim 7 wherein the time increment is selected to be 16.7 ms so that a series of 60 images are produced reflective of 60 positions Pi each second.

9. The method of claim 8 wherein the first and second processes includes applying a Gaussian Filter having a moving window in a range of 12 to 60 positions such that the visualization delay associated with each process is within a respective range of approximately 100 ms to approximately 500 ms.

10. The method of claim 8 wherein the first and second processes include two of the following processes:
a process that includes applying a Gaussian Filter having a moving window of 12 positions such that the visualization delay associated with the other process is approximately 100 ms;
a process that includes applying a Gaussian Filter having a moving window of 20 positions such that the visualization delay associated with the other process is approximately 166 ms; or
a process that includes applying a Gaussian Filter having a moving window of 26 positions such that the visualization delay associated with the other process is approximately 216 ms.

11. The method of claim 8 wherein the images are displayed on a 60 Hz monitor.

12. A method for facilitating the navigation of a distal end of a catheter from a first location within a subject to a second location within the subject with reference to images reflecting relative positions of the distal catheter end as the distal catheter end is displaced from the first location to the second location, the method comprising:
displaying a series of images, each corresponding to a position of the distal catheter end at a successive time increment, as the distal catheter end is displaced from the first location at a time $T_0$ to the second location at a time $T_0$+X seconds based on a selected time increment, including:
sensing the location of the distal end of the catheter at one or more selected rates to produce location data of the catheter corresponding to a position $P_i$ of the catheter distal end at a time $T_i$ for each time increment from $T_0$ to $T_0$+X seconds;
for each position $P_i$, processing the location data corresponding to the position $P_i$ to respectively produce an image $I_i$ reflecting the position of the distal catheter end at the time $T_i$; and
successively displaying each image $I_i$ at a time equal to $T_i$+D, where D is a visualization delay that includes the time spent to process the location data corresponding to the position $P_i$ to produce the image $I_i$; and upon a condition that the catheter distal end is displaced to a selected interim location at a time $T_0+(X-Y)$ seconds between the first and second locations, wherein X−Y represents a difference between X seconds and Y seconds at the selected interim location between the first location at the time $T_0$ to the second location at the time $T_0+X$ seconds, the processing of the location data corresponding to positions $P_i$ to respectively produce images $I_i$ reflecting the position of the distal catheter end at times $T_i$ for each $T_i$ from $T_0$ to $T_0+(X-Y)$ seconds is switched from being performed by a first process associated with a first visualization delay that produces serial images of catheter movement that have a first characteristic to a second process associated with a second different visualization delay that produces serial images of catheter movement that have a second different characteristic to produce images $I_i$ corresponding to positions $P_i$ reflecting the position of the distal catheter end at time $T_i$ for each $T_i$ from $T_0+(X-Y)$ seconds to $T_0+X$ seconds, wherein a process that produces images having heartbeat movement removed includes applying a Gaussian Filter.

13. The method of claim 12 wherein the time increment is selected to be 16.7 ms so that a series of 60 images are produced reflective of 60 positions Pi each second and the images are displayed on a 60 Hz monitor.

14. An apparatus for facilitating the navigation of a distal end of a catheter from a first location within a subject to a second location within the subject with reference to images reflecting relative positions of the distal catheter end as the distal catheter end is displaced from the first location to the second location, the apparatus comprising:

a monitor configured to display a series of images, each corresponding to a position of the distal catheter end at a successive time, as the distal catheter end is displaced from the first location to the second location based on a selected time increment;

sensors configured to sense the location of the distal end of the catheter at one or more selected rates to produce location data of the catheter corresponding to a position $P_i$ of the catheter distal end at a time $T_i$ for each time increment as the distal catheter end is displaced from the first location to the second location;

a processor coupled to the sensors and the monitor and configured to process, for each position $P_i$, the location data corresponding to the position $P_i$ to respectively produce an image $I_i$ reflecting the position of the distal catheter end at the time $T_i$, such that each image $I_i$ is successively displayed at a time equal to $T_i+d$ seconds, where d is a visualization delay that includes the time spent to process the location data corresponding to the position $P_i$ to produce the image $I_i$; and the processor configured to be able to switch the processing of the respective location data from being performed by a first process associated with a first visualization delay that produces serial images of catheter movement that have a predetermined characteristic to a second process associated with a second different visualization delay that produces serial images of catheter movement that have a different characteristic such that:

upon a condition that the catheter distal end is displaced to a selected interim location between the first and second locations, the processing of the location data corresponding to positions $P_i$ to respectively produce images $I_i$ reflecting the position of the distal catheter end at times $T_i$ is switchable from being performed by the first process to being performed by the second process, wherein a process that produces images having heartbeat movement removed includes applying a Gaussian Filter.

15. The apparatus of claim 14 wherein the processor is configured to perform as the first and second processes different process among processes that include:

processes associated with relatively long visualization delays that produce images having heartbeat movement removed when the interim and second locations are within a beating heart of the subject; and processes associated with relatively short visualization delays that produce images that reflect heartbeat movement when the interim and second locations are within a beating heart of the subject; and further including a user operable switch configured to switch the mode of the processor from performing one process to another process among the different processes.

16. The apparatus of claim 15 wherein the time increment is selected to be 16.7 ms so that the processor is configured to produce a series of 60 images reflective of 60 positions Pi each second.

17. The apparatus of claim 16 wherein the processor is configured to perform as the first and second processes different process among processes that include:

a process that produces images having heartbeat movement removed that includes applying a Gaussian Filter having a moving window of 60 positions such that the visualization delay associated with the process is approximately 500 ms; and processes that produces images reflecting heartbeat movement that include applying a Gaussian Filter having a moving window in a range of 12 up to 60 positions such that the visualization delay associated with respective processes is within a respective range of approximately 100 ms up to approximately 500 ms.

18. The apparatus of claim 17 wherein the processes that produce images reflecting heartbeat movement include:

a process that includes applying a Gaussian Filter having a moving window of 12 positions such that the visualization delay associated with the process is approximately 100 ms;

a process that includes applying a Gaussian Filter having a moving window of 20 positions such that the visualization delay associated with the process is approximately 166 ms; and a process that includes applying a Gaussian Filter having a moving window of 26 positions such that the visualization delay associated with the process is approximately 216 ms.

19. The apparatus of claim 16 wherein the monitor is a 60 Hz monitor configured to display images at 60 frames per second.

20. The apparatus of claim 14 further comprising a processor control configured to enable an operator to manually select a specific process or to designate anatomical regions of a subject where respective specified processes are automatically switched to by the processor upon a condition that the distal end of the catheter enters a designated anatomical region.

* * * * *

UNITED STATES PATENT AND TRADEMARK OFFICE
CERTIFICATE OF CORRECTION

PATENT NO. : 11,523,875 B2
APPLICATION NO. : 16/840959
DATED : December 13, 2022
INVENTOR(S) : Gal Hayam et al.

It is certified that error appears in the above-identified patent and that said Letters Patent is hereby corrected as shown below:

In the Specification
In Column 2, Line 17, delete "processes" and insert -- process --, therefor.
In Column 3, Line 4, delete "perform as" and insert -- perform --, therefor.
In Column 4, Line 44, delete "subjects" and insert -- subject's --, therefor.
In Column 8, Line 26, delete "ultrasound 37," and insert -- ultrasound slice 37, --, therefor.
In Column 8, Line 36, delete "in" and insert -- an --, therefor.
In Column 8, Line 47, delete "an exemplary embodiments" and insert -- an exemplary embodiment --, therefor.
In Column 8, Line 52, delete "one" and insert -- on one --, therefor.
In Column 11, Line 33, delete "angle" and insert -- angle of --, therefor.
In Column 11, Line 55, delete "coordinates" and insert -- coordinates) --, therefor.
In Column 12, Line 32, delete "choses" and insert -- chooses --, therefor.

In the Claims
In Column 18, Line 20, in Claim 8, delete "Pi" and insert -- $P_i$ --, therefor.
In Column 18, Line 65, in Claim 12, delete "Ti+D, where D" and insert -- Ti+d, where d --, therefor.
In Column 19, Line 26, in Claim 13, delete "Pi" and insert -- $P_i$ --, therefor.
In Column 20, Line 25, in Claim 16, delete "Pi" and insert -- $P_i$ --, therefor.

Signed and Sealed this
Twenty-eighth Day of May, 2024

*Katherine Kelly Vidal*

Katherine Kelly Vidal
*Director of the United States Patent and Trademark Office*